United States Patent [19]

Bellhouse et al.

[11] Patent Number: 4,758,083
[45] Date of Patent: Jul. 19, 1988

[54] BLOOD MONITORING SYSTEM

[75] Inventors: Brian J. Bellhouse; Sydney M. Pugh; Maxwell R. Derrick, all of Oxfordshire, England

[73] Assignee: Bellhouse Technology Limited, Abingdon, England

[21] Appl. No.: 42,258

[22] Filed: Apr. 24, 1987

Related U.S. Application Data

[62] Division of Ser. No. 790,854, Oct. 24, 1985, Pat. No. 4,675,019.

[30] Foreign Application Priority Data

Oct. 29, 1984 [GB] United Kingdom ............... 8427285

[51] Int. Cl.4 .................. G01N 21/51; G01N 15/02
[52] U.S. Cl. ..................... 356/39; 356/244; 356/427
[58] Field of Search ............. 356/39, 244, 427

[56] References Cited

U.S. PATENT DOCUMENTS

| 2,297,375 | 9/1942 | Vogt | 229/55 |
|---|---|---|---|
| 2,619,277 | 11/1952 | Shumann | 229/55 |
| 3,498,724 | 3/1970 | Hayes et al. | 356/246 |
| 3,698,822 | 10/1972 | Polanyi | 356/246 |
| 4,140,162 | 2/1979 | Gajewski et al. | 150/1 |
| 4,227,814 | 10/1980 | Soodak et al. | 356/410 |
| 4,522,494 | 6/1985 | Bonner | 356/39 |
| 4,657,383 | 4/1987 | Bellhouse | 356/39 |
| 4,682,887 | 7/1987 | Bellhouse et al. | 356/39 |

FOREIGN PATENT DOCUMENTS

| 0141632 | 5/1985 | European Pat. Off. . |
|---|---|---|
| 96516 | 10/1972 | France . |
| 2137037 | 12/1972 | France . |
| WO84/01292 | 4/1984 | PCT Int'l Appl. . |
| 1196374 | 6/1970 | United Kingdom . |

Primary Examiner—Vincent P. McGraw
Attorney, Agent, or Firm—Jeffers, Hoffman & Niewyk

[57] ABSTRACT

A blood monitoring system for the contents of blood bag B utilizes rigid optically clear tablet (16) bonded to rough outer surfaces of the walls of the bag to provide windows through the bag. The bag is gripped by a pair of tongs T the jaws of which have openings to receive the tablets. The outer surfaces of the jaws have ribs (33) and buttons (36) to locate the tongs, and hence the bag, accurately in position in a monitoring device, with the windows (16) in alignment with an optical system of the device.

8 Claims, 6 Drawing Sheets

Fig.5B.
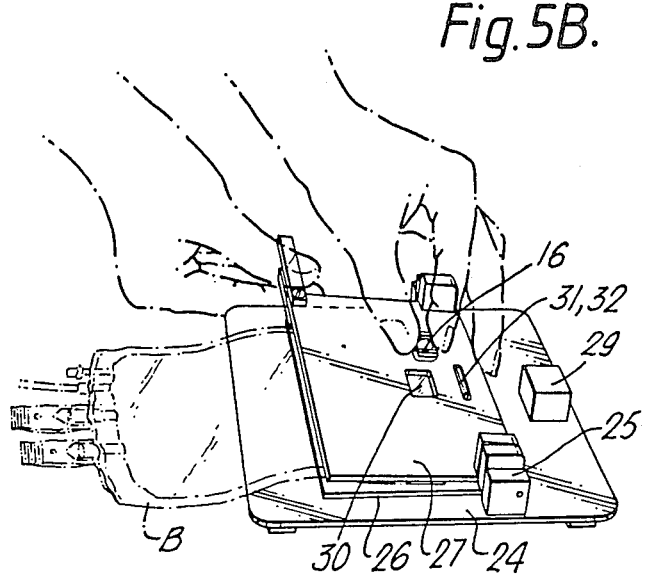
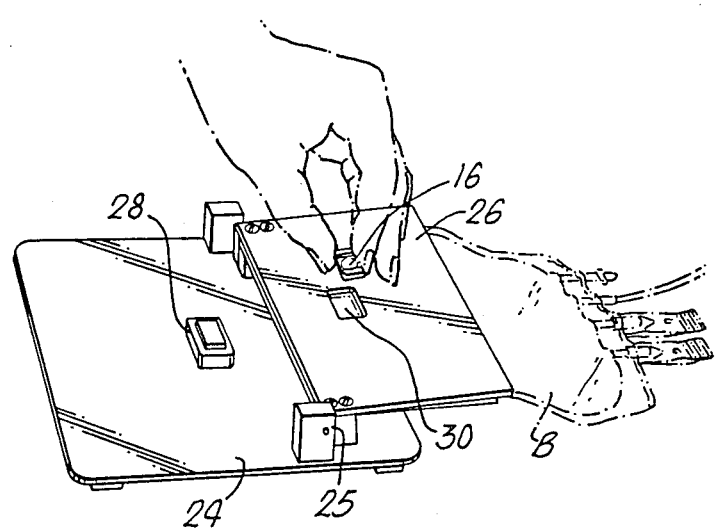
Fig.5C.

# BLOOD MONITORING SYSTEM

This is a division of application Ser. No. 790,854, filed Oct. 24, 1985, now U.S. Pat. No. 4,675,019.

The invention relates to a system for monitoring optically blood components contained in a bag, and particularly to the means whereby a blood bag may be provided with transparent windows, and located precisely in a monitoring device for compatibility with an optical system of the device.

It is now conventional for blood components, such as concentrates of blood platelets in plasma, to be stored in, and administered to patients from, a flexible bag of generally rectangular shape, formed between two sheets of plastics material, which are welded together to provide a comparatively broad seam around their edges. Various holes and slits are formed in this seam for use in supporting the bag at various stages of use. A number of tubes extend through the seam at a nominal top of the bag to provide plumbing connections to the interior of the bag.

A recently developed technique of monitoring non-invasively the viability of blood platelets in a sealed pack is described in copending U.S. patent application Ser. Nos. 666,357 and 666,390. That technique involves passing a beam of light through the pack and depends on collecting light transmitted through the pack as a result of scattering by the platelets.

When this technique is applied to platelets in a conventional bag of the kind referred to above, appreciable scattering of the light occurs owing to the roughness of the outer surfaces of the plastics walls of the bag and this obscures to a large extent the light transmitted through the bag. The surface of the plastics material from which the bag walls are made is rough or textured to avoid adjacent bags sticking together during manufacture. Roughness on the inner surfaces of the bag walls is unimportant as these surfaces are wholly wetted by the blood plasma. However, roughness of the outer surfaces of the bag walls remains a problem which it is one object of the invention to alleviate.

In accordance with the first aspect of the invention, in a blood bag of the kind comprising two walls which are formed by sheets of plastics material sealed together around their edges, at least the outer surfaces of the walls being rough, each of the walls is provided, at least on its outer surface, with means for providing, in use, an optically clear window opposite to that in the other wall.

A bag of this construction may be used in the monitoring technique referred to above by positioning the bag so that the beam of light is passed through the two windows. The scattering which occurs will then be dependent almost entirely on the platelets in the bag and therefore on the parameter being monitored. The optically clear windows may extend fully between both surfaces of the bag walls such that they would exist irrespective of any contents in the bag. However, as explained above, liquids such as blood plasma in the bag will fully wet the inner surface of the bag so that no means need be provided in general for producing an optically clear window at the inner surfaces of the bag walls.

There are a number of ways in which the windows may be provided. For example, the outer surface of each bag wall may be touched, during manufacture, with a hot flat surface to provide a smooth shield surrounded by the rough surface of the rest of the bag wall.

An alternative solution involves sticking an optically clear window to the outer surface of each bag wall. The member may be a patch of optically clear self-adhesive tape, provided that the adhesive is also optically clear. There may however be difficulties in applying the patch accurately in the required position unless the patch is so large that it covers a large proportion of the surface area of the bag wall, with the disadvantage of inhibiting oxygen diffusion through the wall into the bag for nourishing the platelets. Alternatively, the member may be a comparatively rigid tablet of, for example, clear plastics material, which is heat sealed to the bag wall during manufacture of the bag, or stuck to the outer surface of the wall of the finished bag by means of a contact adhesive, which must also be optically clear and biocompatible in case of leeching of components of the adhesive through the normally permeable wall into the contents. An advantage of providing, on the outer surface of each bag wall, a comparatively rigid member is that the members may be applied to the bag more accurately in position, for example using a jig. A further advantage of using comparatively rigid members is that they may be used for locating the bag accurately in a monitoring device so that the windows provided by the tablets are aligned with an optical system for passing a beam of light through the windows and through the contents in the bag.

This use of rigid tablets thus provides the essential link with the second aspect of the invention, which involves the provision of, preferably non-circular, tablets and parts which mate with these tablets when secured to the outer walls of a blood bag, for accurately locating the bag in a monitoring device in alignment with an optical system of the device.

Thus the invention includes a tablet for bonding to a rough outer surface of a wall of a blood bag for providing, in use, an optically clear window through the wall, and adapted for use in locating the blood bag with the window in alignment with an optical system of a monitoring device; the tablet comprising a non-circular moulded body of optically clear plastics material, the tablet having inner and outer faces; a layer of adhesive which is optically clear and biocompatible on the inner face; a release sheet covering the adhesive layer; and raised portions on the outer portions defining a central recessed window portion. The tablets are, in use, peeled from the release sheet and stuck to the bag walls. The central recessed window portion inhibits scratching of the window surface through which the monitoring beam of light will pass.

The invention further includes an applicator for use in bonding two optically clear tablets in alignment with one another to the outer surfaces of respective ones of two opposed walls of a blood bag to provide windows through the bag walls for alignment with an optical system of a monitoring device; the bag being of the kind having, at its bottom, a transverse slit to provide a hanging loop for dispensing contents from the bag; the applicator comprising two plates which are hinged together along one edge so that the plates may be opened away from one another and closed towards one another; one of the plates being provided adjacent to the hinge with a projection for entering the bag slit and locating the bag, in use, between the plates, and each of the plates having in alignment with that in the other of the plates an opening adapted to act as a jig for guiding a tablet into bonding engagement with a corresponding one of the bag walls when the plates are closed around the bag.

The bag, with the attached rigid tablets may be fitted directly into a monitoring device. Alternatively, there may be used tongs including a pair of jaws, for use in straddling and grasping between the jaws a blood bag provided with tablets on the outer surfaces of its opposite walls, the tongs comprising aligned openings in each of the jaws for receiving the tablets, in use as a close fit; and guide means on the outer surfaces of the jaws for locating the tongs and hence, in use, the bag, in a predetermined position in the monitoring device.

The invention also includes a corresponding device for monitoring photoelectrically the contents of a blood bag fitted with the tablets to provide optically clear windows through the bag walls; the device comprising first and second plates which are relatively movable away from one another for insertion, in use of the bag, and towards one another to grasp the bag therebetween; the first plates being provided with a light source and the second plate being provided with a photodetector in alignment with the light source; means cooperating with the tablets for locating the bag between the plates with the windows in alignment with the light source whereby light from the source passes through the windows to the photodetector; ribs projecting from at least one of the plates for pinching together the bag walls to divide the interior of the bag into two parts in opposite sides of the bag, the bag parts being connected by a channel adjacent to the bottom of the bag, the windows being in alignment with the channel; and a piston which is reciprocable to and fro through an opening in one of the first and second plates to squeeze one of the two parts of the bag against the other of the first and second plates to cause contents in the bag, in use, to flow to and fro through the channel; and means connected to the photodetector for processing a variable electrical signal from the photodetector dependent upon the state of the contents of the bag and the flow thereof through the channel, and providing a corresponding indication.

The invention will now be described by way of example with reference to the accompanying drawings, in which:

FIGS. 5A, 5B and 5C are perspective views of an applicator showing successive stages in the application of window tablets to a bag;

Figure 1:
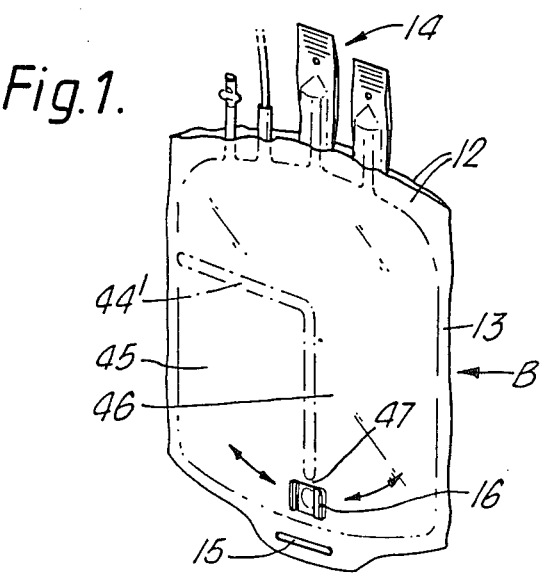
FIG. 1 is a perspective view of a blood bag.
Figure 2:
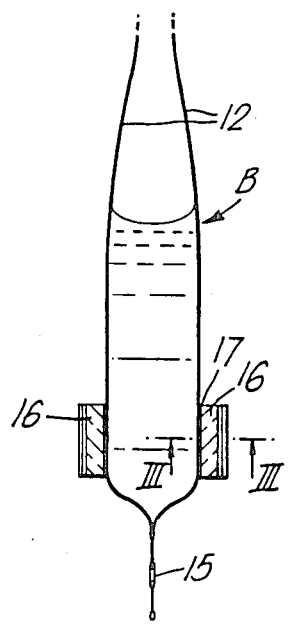
FIG. 2 is a diagrammatic central cross section through the bag.

As shown in FIG. 1, a conventional blood bag B is formed from two sheets 12 of biocompatible plastics material, which are heat welded or otherwise sealed together around their edges to form a seam 13. Conventional plumbing 14 leads through the top of the seam. A slit 15 is formed in the seam 13 at the bottom of the bag, for use in hanging the bag during clinical dispensing of contents of the bag.

Figure 3:
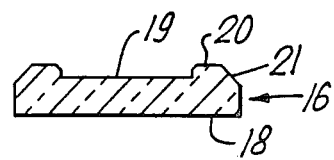
FIG. 3 is a section through a window tablet taken on the line III—III in FIG. 2.

The bag walls 12 are comparatively opaque, owing primarily to the outer surface of the walls being rough. Aligned windows are provided through the walls, adjacent to the bottom of the bag, by means, in each case, of a rigid transparent moulded plastics tablet 16 which is bonded to the outer wall surface by means of an optically clear biocompatible adhesive layer 17. As shown in FIG. 3, each tablet 16 has a flat inner surface 18 for bonding to the bag wall, and an outer surface with a recessed window portion 19 bounded at each end of the tablet by a raised portion 20, which is chamfered at 21 to avoid obstruction when the bag and tablets are subsequently inserted laterally into the monitoring device shown in FIG. 8. The window portion 19 is recessed to avoid scratching of the window surface during handling, or during insertion of the bag into the monitoring device. Each tablet is substantially rectangular in face view and symmetrical about central longitudinal and transverse planes.

Figure 4:
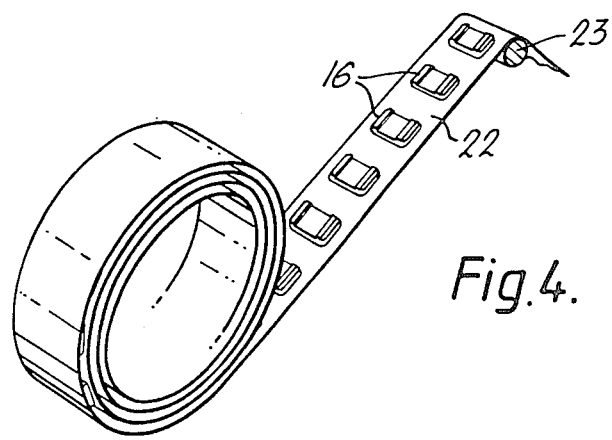
FIG. 4 is a perspective view of a reel of window tablets.

The tablets are supplied in a reel on a backing release strip 22, as shown in FIG. 4 and are peeled off the backing strip to expose the adhesive by drawing the strip under tension over a bar 23. The tablets are then stuck to the bag walls in precisely correct, mutually aligned positions, by means of the applicator shown in FIGS. 5. The applicator comprises a base plate 24 with hinge mountings 25 for a pair of plates 26 and 27 which are thus pivotable towards and away from one another and through substantially 180° relatively to the base 24. The base plate is formed with upstanding anvils 28 and 29, the plates 26 and 27 are provided with aligned rectangular openings 30; and the plate 26 is formed with an upstanding rib 31 with a complementary slot 32 in the plate 27.

Figure 5A:
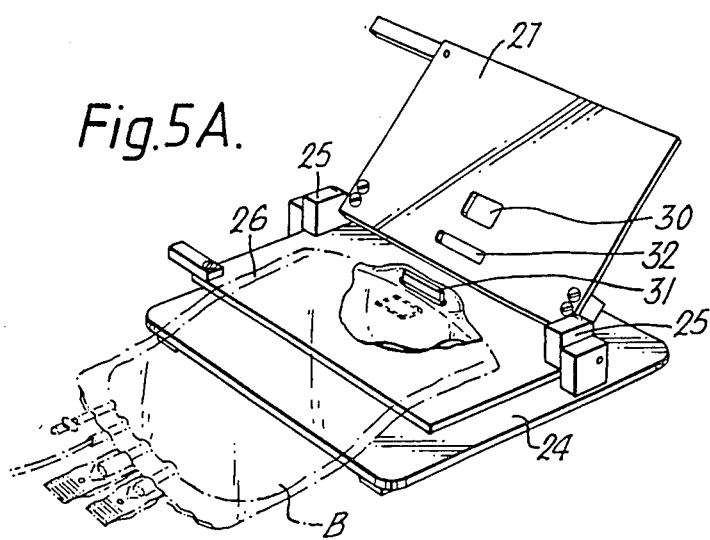

In order to attach the tablets to a bag, the bag is located on the plate 26 with its slit 15 engaging the rib 31, as shown in FIG. 5A. The plate 27 is then closed downwards onto the top of the bag B and plate 26 whereupon a tablet 16, which has been taken from the strip 22 is inserted through the hole 30 in the plate 27 and pressed into bonding engagement with the upper wall of the bag, as shown in FIG. 5B. At this time the anvil 28 projects through the opening 30 in the plate 26 to provide a support for the bag. The two plates 26 and 27 are then swung over to the position shown in FIG. 5C and another tablet 16 is inserted through the opening 30 in the plate 26 and pressed into bonding engagement with the other wall of the bag B. At this time the anvil 29 acts as a support to prevent the previously applied tablet from being pushed down through the opening in the plate 27.

Figure 6:
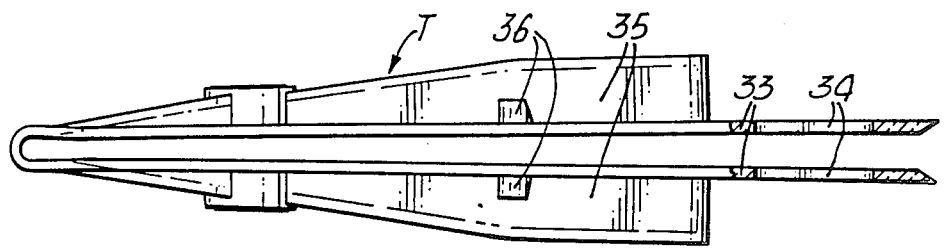
FIG. 6 is a longitudinal cross section through tongs for use with the bag.
Figure 7:
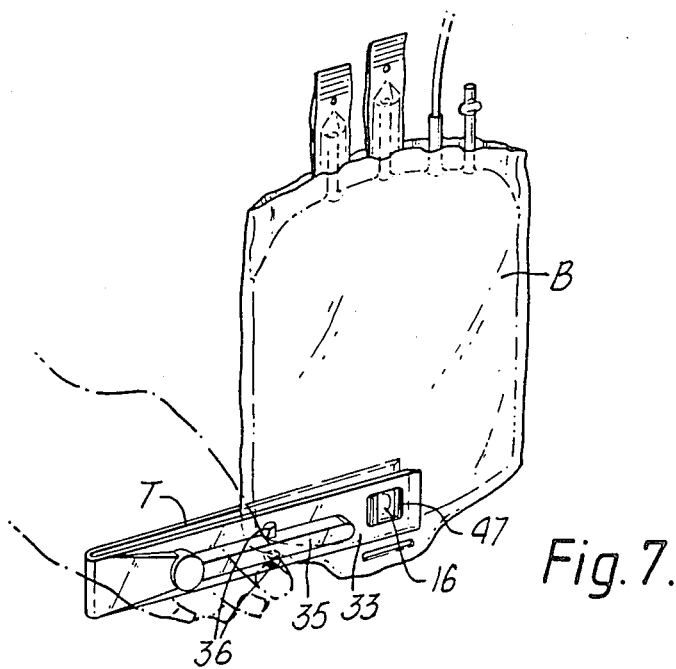
FIG. 7 is a perspective view showing the tongs in association with a bag.
Figure 8:
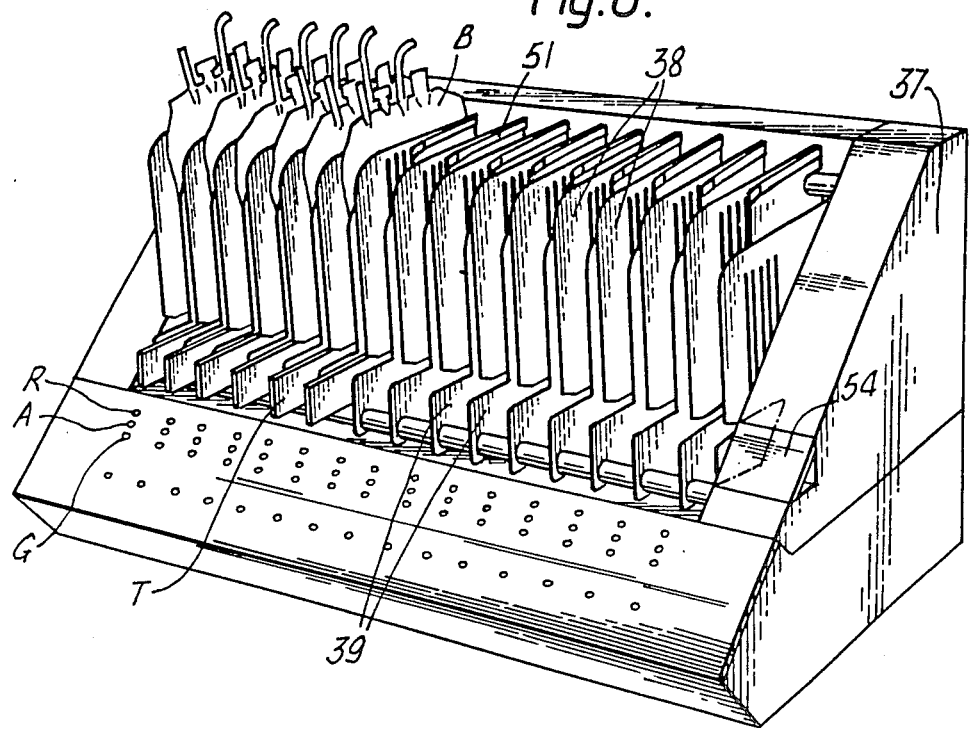
FIG. 8 is a perspective view of a monitoring device.
Figure 9:
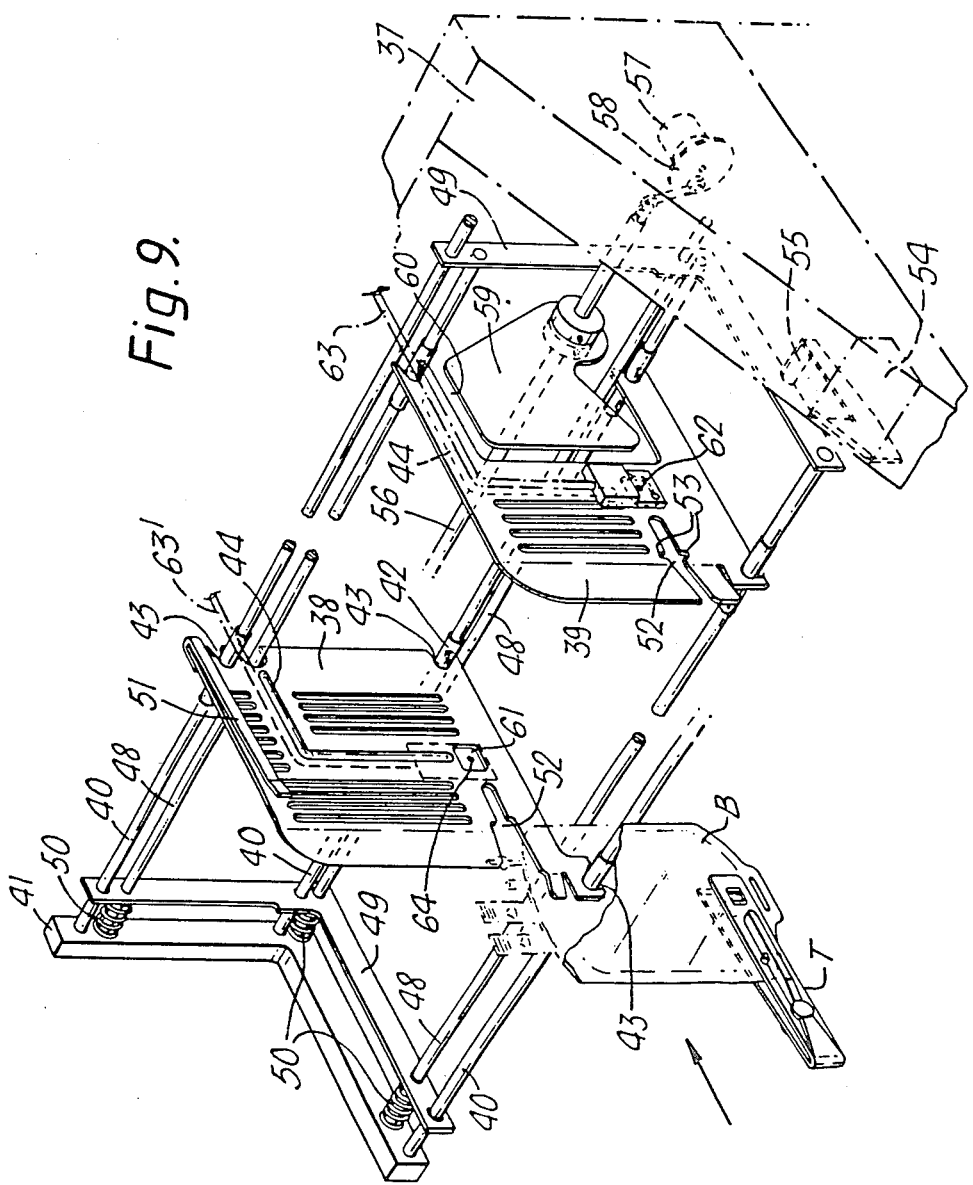
FIG. 9 is a diagrammatic perspective view showing the essential construction and operation of the monitoring device; and, FIG. 10 is a circuit diagram for the monitoring device.

In addition to providing optically clear windows through the walls of the bag B, the tablets 16 provide means for locating the bag accurately in the monitoring device of FIG. 8. For this purpose the bag is used in association with tongs T, as shown in FIGS. 6, 7 and 9. The tongs comprise a pair of mutually flexible jaws 33, each of which is provided adjacent to its free end with a rectangular opening 34, which can receive one of the tablets 16 as a close fit. Each jaw also has on its outer surface an elongate rib 35 and buttons 36, one on each side of the respective rib 35. The bag is inserted between the jaws of the tong, as shown in FIG. 7, and the jaws are slightly closed together to cause the tablets 16 to enter the openings 34.

Figure 10:
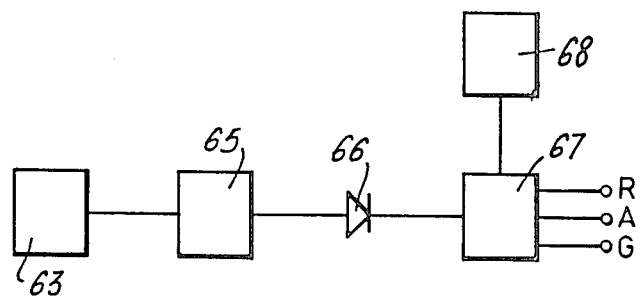

The monitoring device, essentially shown in FIGS. 8 to 10 comprises an open fronted housing 37 containing a series of fifteen monitoring stations, each consisting of a taller fixed plate 38 and a shorter moving plate 39, and a respective display of red, amber and green lights R, A and G. Some of the monitoring stations are shown with bags being in situ. FIG. 9 shows diagrammatically the essential internal constructional features of the device, but only the plates 38 and 39 of one station, and these exaggeratedly spaced for ease of understanding.

The plates 38 and 39, which are slotted to allow circulation of air for gas transfer to and into a bag held between the plates, form part of fixed and movable assemblies. The fixed assembly comprises three horizontal parallel rods 40 which are fixed at each end to stationary L-shaped brackets 41. The fifteen fixed plates 38 are mounted at regular intervals along these rods and spaced from one another by tubular sleeves 42 which encircle the respective rods. The plates are removable, since they engage the rods 40 at peripheral notches 43 so that they can be manipulated off the rods.

The movable assembly comprises three horizontal rods 48, which are parallel to one another and to the rods 40 and which are carried at each end by L-shaped brackets 49, slidable along the rods 40. The fifteen movable plates 39 are fitted onto the rods 48, with intervening spacers 42, similarly to the plates 38 on the rods 40. The movable assembly is urged by compression springs 50 to move so that the movable plates 39 move away from their respective fixed plates 38, for the introduction of bags B.

The bags are inserted into a monitoring station between the plates 38 and 39 by the operator squeezing together the jaws of the tongs T with one hand and holding the top of the bag with the other hand, and offering the bag into the gap between the two plates, as shown by the arrow in FIG. 9. The top of the bag slides into a clip 51 extending across the top of the corresponding fixed plate 38 and the ribs 35 enter open ended slots 52 in the respective plates 38 and 39. As the jaws of the tongs T are released, the buttons 36 enter notches 53 in the edges of the slot 52 in the plate 39 so that the tongs, and hence the bag, are accurately positioned and oriented upright between the plates.

The movable assembly is then moved to bring the plates at each station together by swinging upwards, from the full to the dotted line positions, a fingerpiece 54 whereby a cam 55 engaging the adjacent bracket 49 pushes the movable assembly against the action of the springs 50. In each station at which a bag is present, the bag is then held between the two plates 38 and 39 and particularly between aligned L-shaped rubber ribs 44 mounted on the facing surfaces of the plates. These ribs squeeze the opposed walls 12 of the bag together along a seal line 44' as shown in FIG. 1, so that the interior of the bag is divided into two parts 45 and 46 which are interconnected at the bottom of the bag by a channel 47 positioned between the windows provided by the tablets 16.

The device also includes a further rod 56, parallel to the rods 40 and 48, and continually reciprocatable with a frequency of about 2 Hz, longitudinally by means of a motor 57 and crank 58. Fixed on the rod 56 are fifteen pressers 59 one for each monitoring station, whereby each presser 59 continually moves to and fro through an opening 60 in the respective movable plate 39. The presser 59 continually squeezes the part 45 of a bag in that station against the other plate 38 so as to displace the contents of the bag through the channel into the part 46, and then when the squeezing by the presser is released, allowing the contents to flow back through the channel 47 into the part 45 again under the differential hydrostatic pressure across the channel 47, as indicated by the arrows in FIG. 1. When a bag contents are blood platelets, this beneficially keeps the platelets in continual agitation, which is necessary for healthy storage of the platelets.

More importantly, in the context of monitoring the viability of the blood platelets, the continual to and fro movement of the platelets through the channel 47, and their corresponding repeated change of direction, causes a fluctuation in the orientation of the platelets in the channel, specifically from a generally oriented configuration at maximum flow velocity to semi-random orientation upon reversal of the direction of flow. This fluctuation in the orientation of the blood platelets causes a fluctuation in light transmitted through the platelets in the bag. When a bag is properly oriented relatively to the plates 38 and 39 at a monitoring station, as a result of the operation of the ribs 35 and buttons 36, the windows provided by the buttons 16 attached to the bag will be in alignment with openings 61 in the plates 38 and 39. Behind the opening 61 in the plate 39 is mounted a light emitting diode 62, connected to an energy source via a lead 63. Behind the opening 61 in the plate 38 is mounted a photodetector 64 from which an electrical output signal is led to a signal processing circuit via another lead 63'. As the platelets flow to and fro through the channel 47, the photodetector 64 receives a fluctuating amplitude of light from the LED 62 and produces a corresponding fluctuating signal in the line 63'.

As diagrammatically shown in FIG. 10, this signal from the photodetector 64 is passed through an AC coupling 65, which extracts the AC component of the signal, and this is partially rectified by a diode 66. The amplitude of the resulting DC signal, corresponding to the amplitude of the fluctuation in the signal from the photodetector 64, is compared in a comparator 67 with a datum level set by a control 68 related to the level corresponding to acceptable platelet viability. As explained in our earlier copending applications, the amplitude of the fluctuating signal from the photodetector 64 decreases by a factor of 5 or more as healthy platelets die. The output of the comparator 67 energises one of the respective red lamp R, amber lamp A, or green lamp G, on the device display, depending upon whether the comparison indicates that the platelets in the bag under test are in healthy condition, average condition or poor condition.

Although the invention has been described in the context of a blood bag for a concentrate of blood platelets in plasma, the invention is applicable to equipment for bags containing other blood components, where monitoring of the contents by passage of light is necessary.

We claim:

1. A device for monitoring photoelectrically the contents of a blood bag of a kind comprising two opposed walls, a pair of aligned, non-circular, optically clear tablets bonded to the outer surfaces of respective ones of said walls to provide optically clear windows through said walls; said device comprising first and second plates which are relatively movable away from one another for insertion, in use of said bag, and towards one another to grasp said bag therebetween;

said first plate being provided with a light source and said second plate being provided with a photodetector in alignment with said light source; means cooperating with said tablets for locating said bag between said plates with said windows in alignment with said light source whereby light from said source passes through said windows to said photodetector; ribs projecting from at least one of said plates for pinching together said bag walls to divide the interior of said bag into two parts in opposite sides of said bag, said bag parts being connected by a channel adjacent to the bottom of said bag, said windows being in alignment with said channel; and a piston which is reciprocatable to and fro through an opening in one of said first and second plates to squeeze one of said two parts of said bag against the other of said first and second plates to cause contents in said bag, in use, to flow to and fro through said channel; and means connected to said photodetector for processing a variable electrical signal from said photodetector dependant upon the state of the contents of said bag and said flow thereof through said channel, and providing a corresponding indication.

2. A device according to claim 1, wherein said locating means comprise tongs with a pair of jaws for straddling and grasping said bag therebetween, said jaws being provided with openings adapted to receive said tablets, in use as a close fit, to locate said bag in a predetermined position relatively to said tongs, and means to locate said tongs relatively to said plates to locate said tongs and hence said bag in a predetermined position relatively to said plates.

3. A device according to claim 2, wherein said means for locating said tongs relatively to said plates comprise ribs projecting from and extending longitudinally along outer surfaces of said jaws and engageable in aligned open ended slots in said plates, and at least one button projecting from an outer surface of a respective one of said jaws for engagement in a corresponding notch in a respective one of said plates to interfere with subsequent withdrawal of said ribs from their said slots.

4. A multi-station device according to claim 1, wherein there are a plurality of said pairs of plates comprising, for each of said stations, a fixed plate and a movable plate, said movable plates being interleaved between said fixed plates; and, for each station a separate piston, said pistons all being moved to and fro simultaneously by a common motor and driving means.

5. A device according to claim 4, wherein said fixed and movable plates, and said pistons, are mounted on a series of parallel rods.

6. A device according to claim 4, wherein said movable plates are coupled together to move simultaneously towards and away from their respective fixed plates; and there are spring means for urging said movable plates away from said fixed plates and a fingerpiece coupled to said movable plates for moving said movable plates towards said fixed plates against the action of said spring.

7. A device according to claim 1, wherein said indicating means comprises red, amber and green lights which are selectively illuminated by the processing means to indicate that the contents of said bag are in poor condition, moderate condition, or good condition respectively.

8. A device according to claim 1, wherein said signal processing means comprises an AC coupling for extracting an AC signal from the output from said photodetector, a diode for producing a partial rectification of said AC signal, a comparator for comparing the amplitude of said partially rectified AC signal with a datum amplitude, and an indicator for indicating the relationship between amplitudes.

* * * * *